(12) United States Patent
Justin et al.

(10) Patent No.: US 7,799,086 B2
(45) Date of Patent: Sep. 21, 2010

(54) MODULAR BONE IMPLANT, TOOLS, AND METHOD

(75) Inventors: Daniel F. Justin, Logan, UT (US); E. Marlowe Goble, Alta, WY (US); Daniel J. Triplett, Providence, UT (US); Robert A. Hodorek, Warsaw, IN (US)

(73) Assignee: Zimmer Technology, Inc., Waraw, IN (US)

( * ) Notice: Subject to any disclaimer, the term of this patent is extended or adjusted under 35 U.S.C. 154(b) by 604 days.

(21) Appl. No.: 10/682,101

(22) Filed: Oct. 9, 2003

(65) Prior Publication Data

US 2004/0073315 A1  Apr. 15, 2004

Related U.S. Application Data

(63) Continuation-in-part of application No. 10/369,331, filed on Feb. 18, 2003, now Pat. No. 7,182,786, which is a continuation-in-part of application No. 10/132,668, filed on Apr. 25, 2002, now abandoned.

(51) Int. Cl.
*A61F 2/38* (2006.01)
(52) U.S. Cl. ............... 623/20.32; 623/20.34; 606/99
(58) Field of Classification Search .......... 606/91, 606/99, 100, 205–212; 623/20.14–20.15, 623/20.32–20.34, 20.18
See application file for complete search history.

(56) References Cited

U.S. PATENT DOCUMENTS

| | | | |
|---|---|---|---|
| 2,725,878 A | 12/1955 | Reiter | |
| 4,318,316 A * | 3/1982 | Guilliams | 81/426.5 |
| 4,936,853 A | 6/1990 | Fabian | |
| 4,938,769 A | 7/1990 | Shaw | |
| 5,020,519 A * | 6/1991 | Hayes et al. | 606/237 |
| 5,147,407 A | 9/1992 | Taeger | |
| 5,290,313 A | 3/1994 | Heldreth | |
| 5,308,357 A * | 5/1994 | Lichtman | 606/205 |
| 5,361,782 A * | 11/1994 | Bauer | 128/898 |
| 5,364,397 A | 11/1994 | Hayes et al. | |
| 5,405,398 A | 4/1995 | Buford, III | |
| 5,609,641 A | 3/1997 | Johnson | |
| 5,609,645 A | 3/1997 | Vinciguerra | |
| 5,674,225 A | 10/1997 | Muller | |
| 5,732,992 A * | 3/1998 | Mauldin | 294/119.1 |
| 5,814,097 A | 9/1998 | Sterman et al. | |
| 5,849,015 A | 12/1998 | Haywood et al. | |
| 5,944,723 A * | 8/1999 | Colleran et al. | 606/88 |
| 5,976,147 A | 11/1999 | LaSalle | |
| 6,110,179 A | 8/2000 | Flivik et al. | |

(Continued)

FOREIGN PATENT DOCUMENTS

EP  0 552 950 B1  9/1996

(Continued)

OTHER PUBLICATIONS

The Partial European Search Report issued Aug. 5, 2009 in related European Application No. EP08017942.7.

*Primary Examiner*—Eduardo C Robert
*Assistant Examiner*—Christina Negrelli
(74) *Attorney, Agent, or Firm*—Baker & Daniels LLP

(57) ABSTRACT

Modular bone implants, means of assembly, and their method of use are presented.

8 Claims, 11 Drawing Sheets

U.S. PATENT DOCUMENTS

| | | | |
|---|---|---|---|
| 6,113,605 | A | 9/2000 | Storer |
| 6,159,217 | A * | 12/2000 | Robie et al. ............... 606/88 |
| 6,214,052 | B1 | 4/2001 | Burkinshaw |
| 6,238,435 | B1 | 5/2001 | Meulink et al. |
| 6,306,172 | B1 | 10/2001 | O'Neil |
| 6,585,771 | B1 | 7/2003 | Buttermilch et al. |
| 6,669,728 | B2 | 12/2003 | Despres et al. |
| 6,926,732 | B2 | 8/2005 | Derus et al. |
| 2002/0072799 | A1 | 6/2002 | Despres, III et al. |
| 2002/0161375 | A1 | 10/2002 | Ralph et al. |
| 2003/0158606 | A1 | 8/2003 | Coon et al. |
| 2003/0204263 | A1 | 10/2003 | Justin et al. |
| 2003/0229355 | A1 * | 12/2003 | Keller ..................... 606/99 |
| 2003/0229357 | A1 | 12/2003 | Dye |
| 2004/0010262 | A1 | 1/2004 | Parkinson et al. |
| 2004/0127910 | A1 | 7/2004 | Pubols et al. |
| 2004/0249467 | A1 | 12/2004 | Meyers et al. |
| 2005/0004673 | A1 | 1/2005 | Kluger |
| 2005/0049623 | A1 | 3/2005 | Moore et al. |
| 2005/0090824 | A1 | 4/2005 | Shluzas et al. |
| 2005/0203631 | A1 | 9/2005 | Daniels et al. |
| 2005/0203632 | A1 | 9/2005 | Daniels |
| 2005/0283250 | A1 | 12/2005 | Coon et al. |
| 2005/0283251 | A1 | 12/2005 | Coon et al. |
| 2005/0283252 | A1 | 12/2005 | Coon et al. |
| 2006/0116768 | A1 * | 6/2006 | Krueger et al. ........... 623/17.14 |
| 2007/0162145 | A1 | 7/2007 | Justin et al. |
| 2008/0147203 | A1 | 6/2008 | Cronin |
| 2009/0187251 | A1 | 7/2009 | Justin et al. |

FOREIGN PATENT DOCUMENTS

| | | |
|---|---|---|
| EP | 0 956 836 A | 11/1999 |
| EP | 0 956 836 A1 | 11/1999 |
| EP | 1059070 | 12/2000 |
| EP | 1449500 A2 | 8/2004 |
| FR | 2627983 | 9/1989 |
| FR | 2 748 389 | 11/1997 |
| FR | 2799115 A1 | 4/2001 |
| WO | WO 98/08467 | 3/1998 |
| WO | WO 00/72784 | 12/2000 |
| WO | WO 02/07647 | 1/2002 |

* cited by examiner

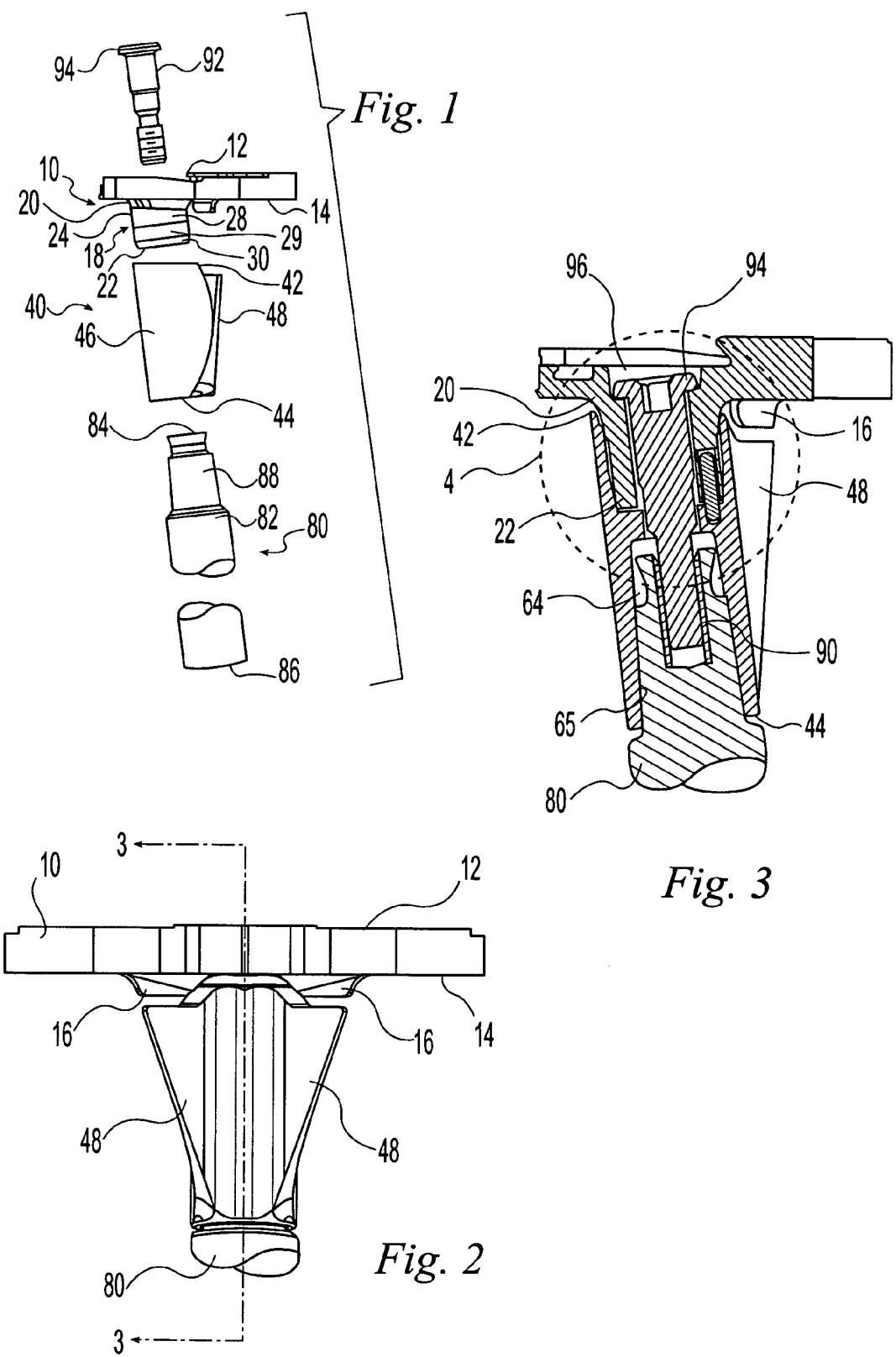

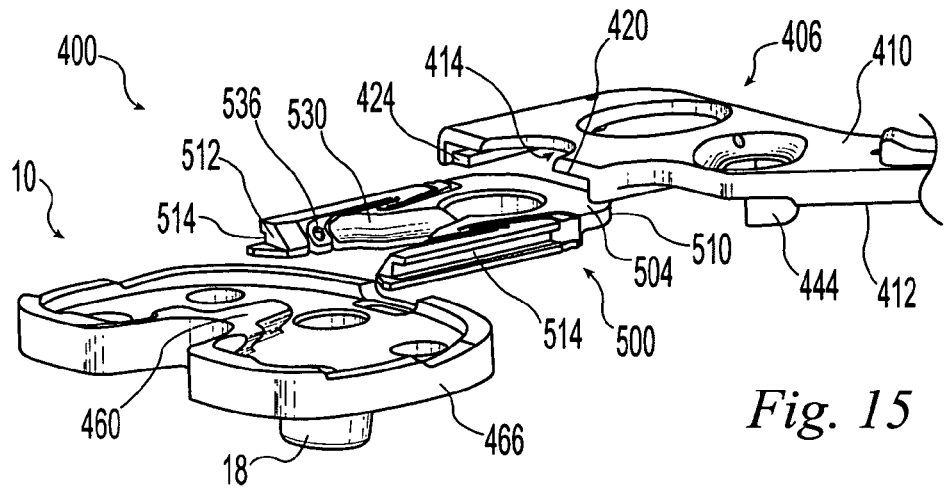
Fig. 15
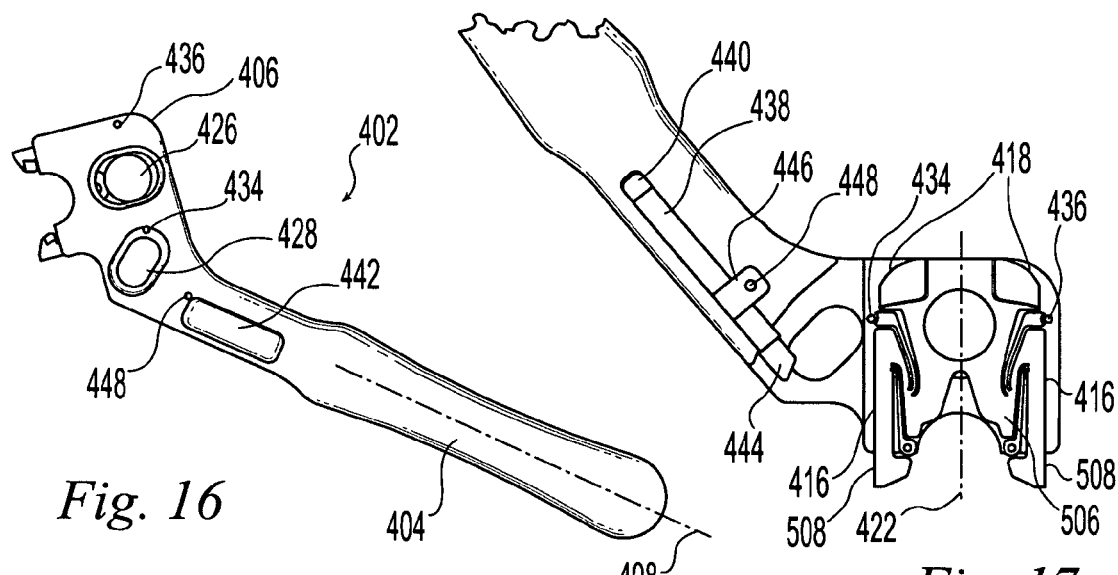
Fig. 16
Fig. 17
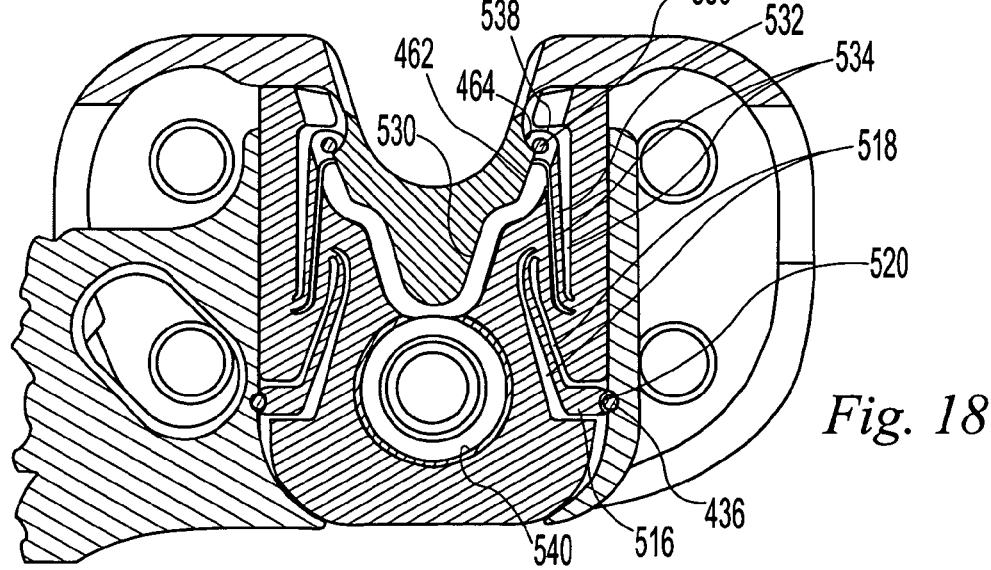
Fig. 18

MODULAR BONE IMPLANT, TOOLS, AND METHOD

CROSS-REFERENCE TO RELATED APPLICATIONS

This application is a continuation-in-part of U.S. application Ser. No. 10/369,331, filed Feb. 18, 2003, now U.S. Pat. No. 7,182,786 which is a continuation-in-part of U.S. application Ser. No. 10/132,668, filed Apr. 25, 2002 now abandoned.

BACKGROUND

The present invention relates to modular bone implants, instruments for handling and assembling the implants, and their method of use.

In order to improve the outcome of joint replacement surgery, attempts have been made to reduce the amount of soft tissue disruption during the procedure by developing minimally invasive surgical techniques. This has lead to smaller incisions with less access to place the prosthetic joint components.

SUMMARY

The present invention provides a modular implant with a mechanism for securing the modular components together. A set of instruments is presented for holding and assembling the modular components together. The implant and instruments are suitable for any type of surgical approach. However, the implant and instruments have features that facilitate minimally invasive surgical procedures.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 1 is an exploded side elevation view of an illustrative embodiment of a bone implant according to the present invention;

FIG. 2 is a rear elevation view of the illustrative embodiment of FIG. 1;

FIG. 3 is a side sectional view of the illustrative embodiment of FIG. 1 taken along line 3-3 of FIG. 2;

FIG. 15 is an exploded perspective view of a tibial tray component holding instrument usable with the instrument of FIG. 9 according to the present invention;

FIG. 16 is a top plan view of the instrument of FIG. 15;

FIG. 17 is a bottom plan view of the instrument of FIG. 15;

FIG. 18 is a section view of the instrument of FIG. 15;

DESCRIPTION OF THE ILLUSTRATED EMBODIMENTS

Figure 4:
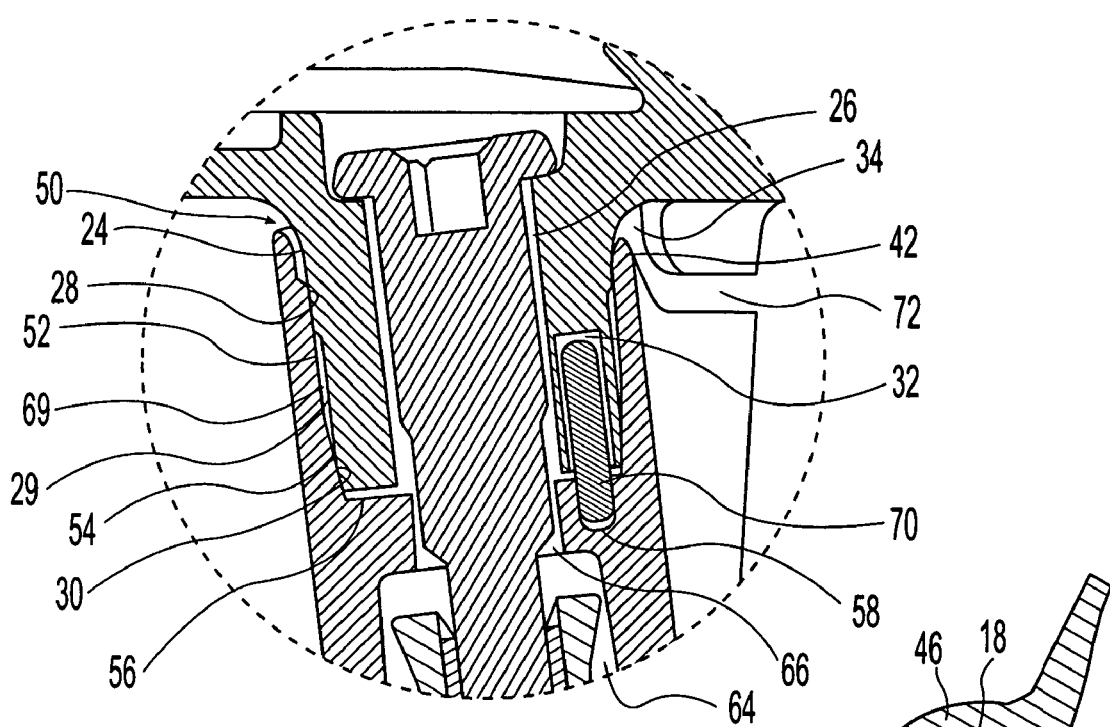
FIG. 4 is a detail view of the sectional view of FIG. 3.

The present invention is applicable to any bone implant in which modularity is advantageous. Examples include joint prostheses for the knee, hip, shoulder, elbow, ankle, and wrist. Such prostheses are implanted by first making an incision near the joint to access the joint space, cutting away the articulating bone ends to be replaced, and seating the prostheses on and/or in the cut bone ends. FIGS. 1-8 depict an illustrative tibial knee prosthesis used to describe the various aspects of the invention.

A tibial prosthesis 2 includes separate tray 10, keel 40, and stem 80 components able to be joined together to form a desired joint prosthesis configuration for replacing the articular surface of the proximal tibia. The tray 10 includes generally planar top 12 and bottom 14 surfaces. The top surface 12 is configured to receive a bearing surface (not shown), such as a polyethylene bearing surface, as is known in the art. The bottom surface 14 is configured to sit on the cut end of the proximal tibia. As best seen in FIG. 2., one or more fins 16 extend radially along the bottom surface 14 and project downwardly from the bottom surface. The fins 16 are received in grooves cut in the proximal tibia to provide rotational resistance to the prosthesis. The fins 16 also serve to strengthen the tray 10 by increasing the bending moment of inertia of the tray 10. Where further stability is desired, the tray 10 provides for the modular attachment of additional components via a boss 18 extending downwardly from the bottom surface 14. The boss 18 includes a top end 20 joined to the bottom surface 14 of the tray 10, a freely projecting bottom end 22, and an axis extending from the top end 20 to the bottom end 22. An outer wall 24 defines the exterior of the boss 18 and an inner bore 26 (FIG. 4) extends from the top end 20 to the bottom end 22. The outer wall 24 includes a cylindrical mating portion 28, a tapered mating portion 30, and a relieved, non-mating portion 29 therebetween. An alignment hole 32 (FIG. 4) is formed in the bottom end 22 and extends upwardly between the outer wall 24 and the inner bore 26. The fins 16 can attach to the boss 18, or they can stop short of the boss 18 to leave a gap 34. Fixation holes 36 may be formed through the tray 10 from the top surface 12 to the bottom surface 14 to accept bone screws (not illustrated) for securing the tray 10 to the proximal tibia.

Figure 5:
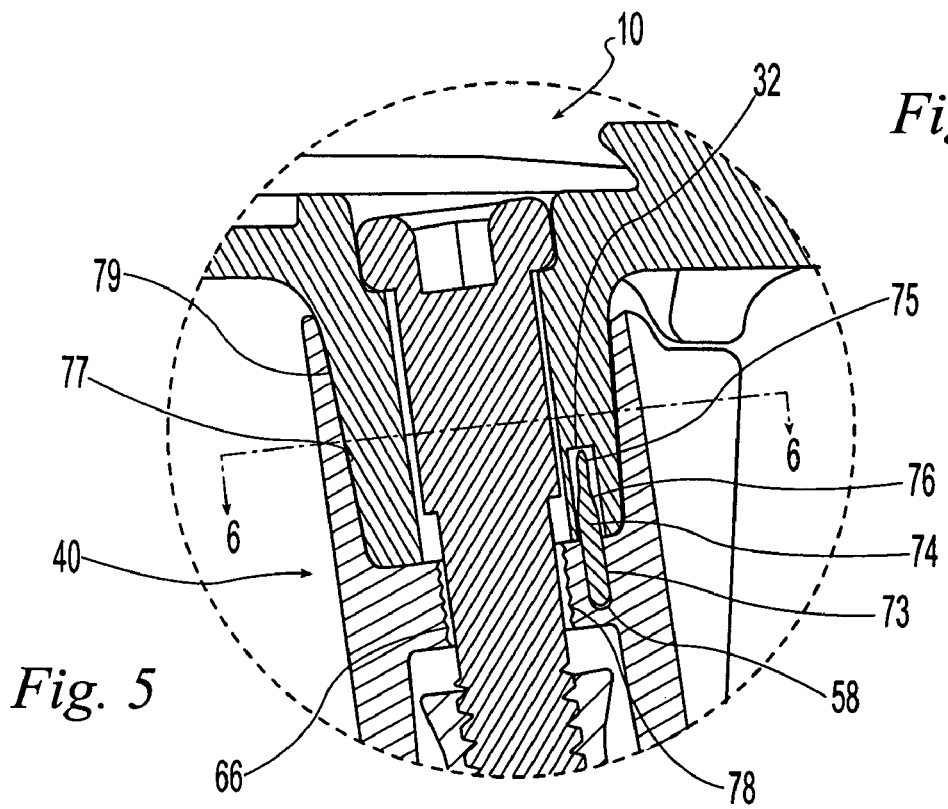
FIG. 5 is a detail view similar to FIG. 4 showing alternative pin and junction configurations.
Figure 7:
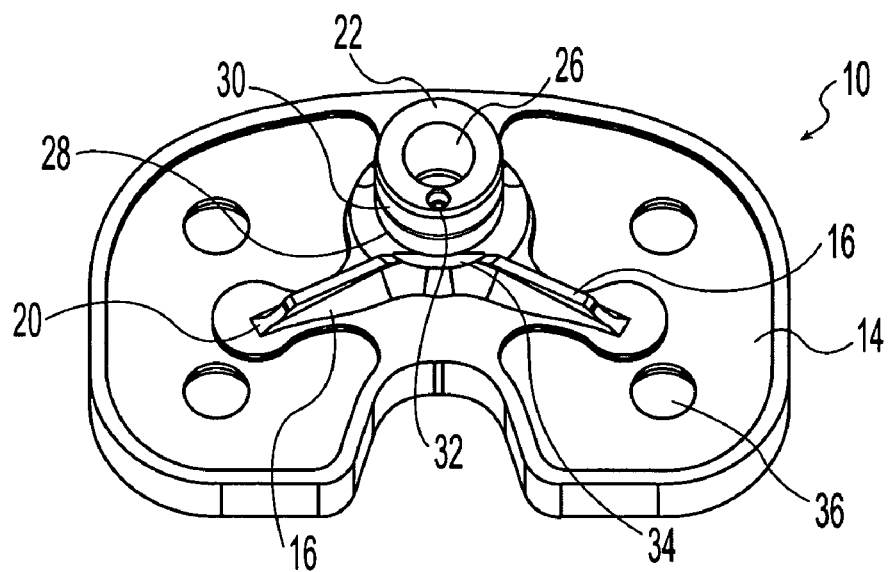
FIG. 7 is a bottom perspective view of the tray of the illustrative embodiment of FIG. 1.
Figure 8:
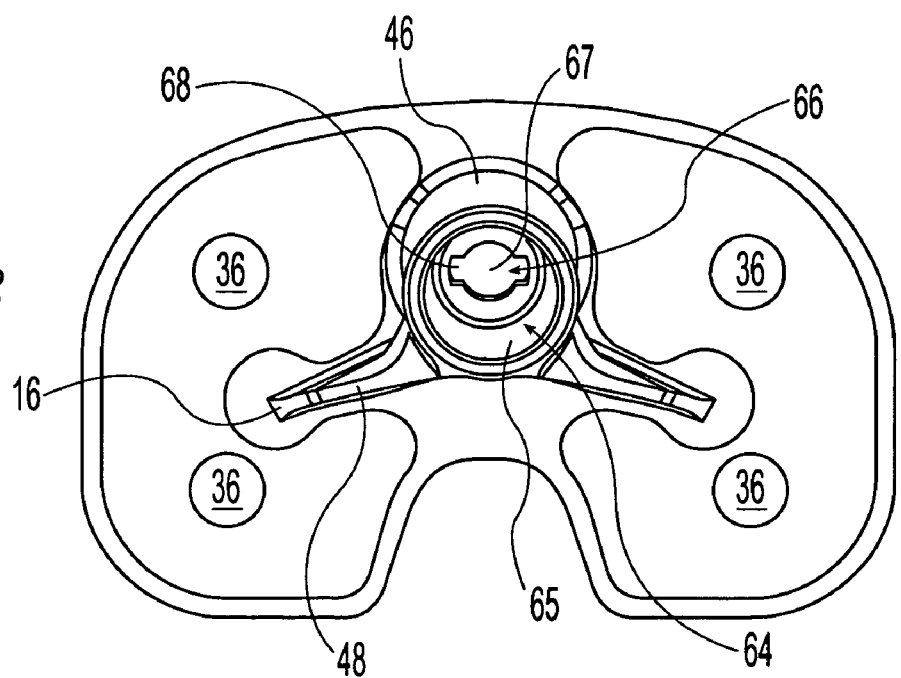
FIG. 8 is a bottom plan view of the tray and keel of the illustrative embodiment of FIG. 1 assembled together.
Figure 9:
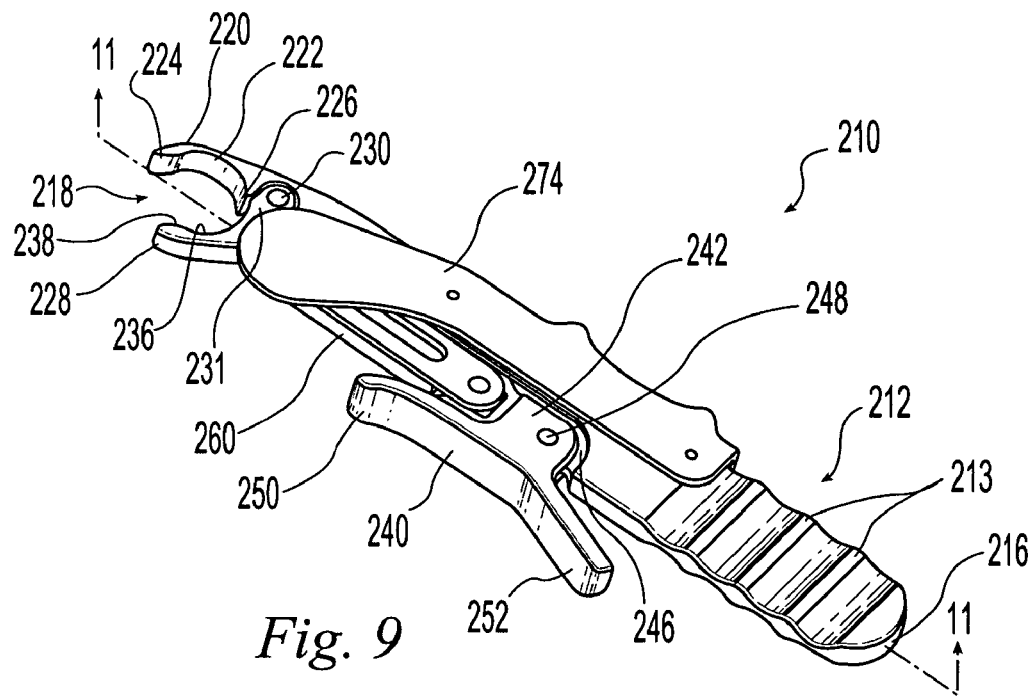
FIG. 9 is a perspective view of a tibial keel component holding instrument according to the present invention with the cover retracted.
Figure 10:
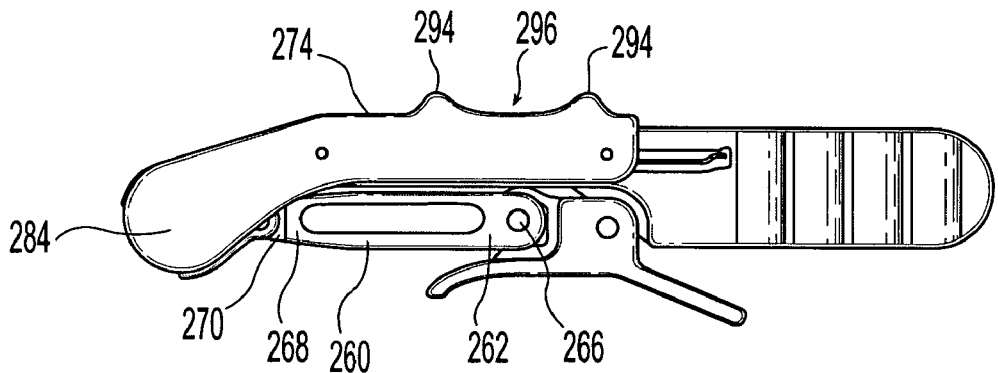
FIG. 10 is a top plan view of the instrument of FIG. 9 with the cover extended.
Figure 11:
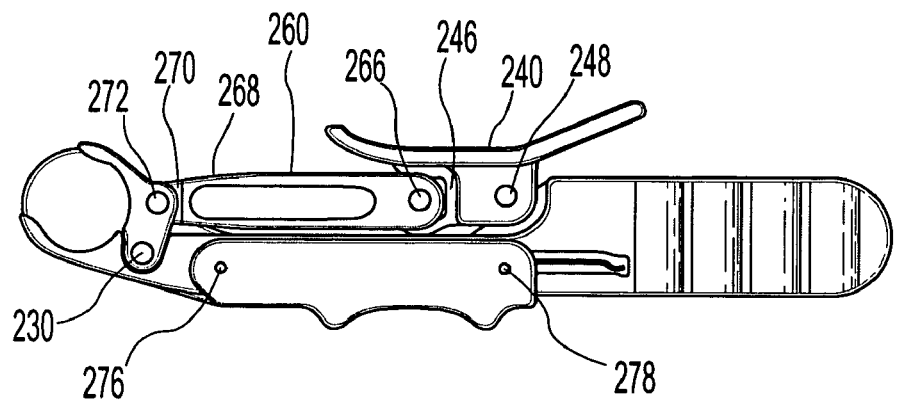
FIG. 11 is a bottom plan view of the instrument of FIG. 9 with the cover extended.

An extension can be mounted on the tray 10 to increase the stability of the tibial prosthesis on the bone. Such an extension can take the form of a stem, a fluted stem, or a keel. The extension can be symmetric or asymmetric. In the illustrative embodiment, a keel 40 is mated to the boss 18 to increase both the rotational and bending stability of the tibial prosthesis on the bone. The keel 40 includes an elongate body having a top end 42 and a bottom end 44 with an axis extending between them, and an outer wall 46. The keel includes at least one fin 48 extending axially along the outer surface 46 and projecting radially outwardly. The keel 40 includes a first axial bore 50 extending downwardly from the top end 42 and having a bore wall including a cylindrical mating portion 52, a tapered mating portion 54, and an end wall 56. An alignment hole 58 is formed in the end wall 56 and extends downwardly. The keel 40 further includes a second axial bore 64 extending upwardly from the bottom end 44 and comprising a tapered side wall 65. A keyed portal 66 communicates between the first 50 and second 64 axial bores. As best seen in FIG. 8, the portal 66 includes a circular central opening 67 and side slots 68 forming a bayonet engageable member. Alternately, the portal 66 can be threaded 78 (as shown in FIG. 5) for engaging a threaded member.

The keel 40 engages the tray 10 with the boss 18 received in the first axial bore 50, the tapered portion 30 of the boss seating on the tapered portion 54 of the bore 50, and the cylindrical portion 28 of the boss being received by the cylindrical portion 52 of the bore in press-fit relationship to form a male/female junction between the tray 10 and keel 40. The tapered portions 30, 54 aid in aligning the components as they are brought together. The cylindrical press-fit locks the components together. The cylindrical press-fit also provides a fluid tight seal to prevent material from migrating past the press-fit into or out of the junction. In the illustrative embodiment, the relieved portion 29 of the boss 18 results in a circumferential gap 69 between the boss 18 and first axial bore 50 lying between the cylindrical 28, 52 and tapered 30,54 portions of the junction. The tray 10 and keel 40 can be aligned by providing an alignment pin 70 in one of the alignment holes 32, 58. In the illustrative embodiment, the keel alignment hole 58 is slightly smaller than the pin 70 and the pin 70 is pressed into it. The tray alignment hole 32 is slightly larger than the pin 70. As the components are brought together, they are prevented from seating until the tray alignment hole 32 engages the pin 70. Where a gap 34 exists between the boss 18 and fins 16, the top end 42 of the keel 40 can extend further up and fit into the gap 34 as shown in FIG. 4.

The pin 70 in the illustrative embodiment of FIG. 4 is cylindrical over its length. FIG. 5 shows an alternative configuration in which a pin 73 has a first portion 74 and a second portion 75 having a smaller cross sectional dimension than the first portion 74. The end of the pin adjacent the first portion 74 is fixed in one of the alignment holes 32, 58 in the components and the pin 73 extends outwardly for engagement with the other of the alignment holes 32, 58. In the illustrative embodiment, the first 74 and second 75 portions are cylindrical and a tapered portion 76 connects them. Also, in the illustrative embodiment, the end of the pin 73 adjacent the first portion 74 is pressed into the alignment hole 58 of the keel 40 and the pin 73 projects upwardly toward the opening of the axial bore 50 in the keel 40. The second portion 75 has a smaller diameter than the first portion 74. As the components are brought together, they are prevented from seating until the tray alignment hole 32 engages the pin 73. The smaller diameter of the second portion 75 allows the pin 73 to engage the tray alignment hole 32 even if the tray 10 and keel 40 are partially out of alignment. As the components are further engaged, the tapered portion 76 presses against the side of the tray alignment hole 32 causing the components to rotate until they are in final alignment as the first portion 74 engages the tray alignment hole 32.

The junction of the present invention makes use of a press-fit which is advantageous over Morse taper-type arrangements used alone. The press fit allows the components to slide together in tight frictional engagement to create a fluid-tight seal and strong resistance to dislocation. The practicalities of machining result in a press-fit having a band, or area, of contact whereas a taper typically has line contact between the mating parts. The press-fit therefore provides a better seal and is more likely to prevent material from migrating across the press-fit boundary. Furthermore, the press-fit locking arrangement is not dependent on precise axial positioning between the components and therefore allows them to be positioned axially at a desired location, once initial press-fit engagement has been achieved. While a cylindrical press fit has been shown and lends itself to precise manufacturing, other cross-sectional shapes can be used in a sliding press-fit according to the invention. The junction also utilizes a taper engagement which provides for centering of the components during assembly and a positive stop to seating as the tapered portions bottom on one another. When the taper is fully seated, it provides increased bending strength to the junction due to the axial distance between the press fit and taper contacts. As shown in FIG. 4, the press-fit 28, 52 and tapered 30, 54 portions are spaced apart axially as far as possible to maximize the bending strength of the junction. The illustrative taper is greater than 3° to facilitate manufacturing of a taper with a predictable seating depth. However, the taper can be a locking taper to provide further locking strength. Because the press-fit permits continued axial translation during assembly after it is engaged, the tapered portion of the junction can be locked after the press-fit has been engaged. A locking taper locks the junction axially and rotationally due to high frictional forces. An example of such a locking taper is the Morse taper. Typically, a locking taper would be on the order of 1.5-3°.

Notwithstanding the advantages of combining a press fit and a taper, the junction may also include only a taper or only a press fit. FIG. 5 illustrates a junction in which a taper alone is used. In the illustrative embodiment of FIG. 5, the keel 40 includes a female taper 77 and the tray 10 includes a male taper 79. The taper may be a locking taper.

Figure 6:
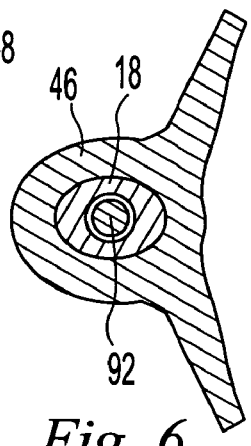
FIG. 6 is a sectional view taken along line 6-6 of FIG. 5 and showing an optional cross sectional shape for the male/female junction.

The junctions shown in FIGS. 3-5 may have circular cross-sections or non-circular cross-sections such as oval, square, elliptical or oblong. A junction having a non-circular cross-section will form a positive lock rotationally due to the radial mating of the non-circular cross sectional portions of the junction. For example, an axial self-locking taper also having an oval cross-section will allow for rough rotational alignment of the two components when the components are loosely fit together and axial tapered locking and rotational positive locking once the components are fully pressed together as shown in FIG. 6.

When assembled, the tray fins 16 and keel fins 48 are generally aligned with one another from top to bottom to project as a single fin, as best seen in FIG. 8. However, as best seen in FIG. 4, when the tray and keel are fully assembled, there remains an axial gap 72 between the fins 16, 48 so that they do not touch. In the illustrative embodiment, the first axial bore is arranged with the cylindrical press fit portion 52 above the tapered portion 54 and locking pin 70. With this arrangement, and the axial spacing 72 of the fins 16, 48, there is no contact between the tray 10 and keel 40 outside of the junction. Any particles that may be produced by contact between the components are sealed in the junction so that they cannot migrate upward into the joint space. While it is within the scope of the invention to form the tapered portions above the cylindrical portions to provide the centering and locking functions, such an arrangement does not provide the same sealing characteristics.

A stem 80 (FIGS. 1-3) can be combined with the tray 10 and keel 40 assembly to provide further bending stability to the tibial prosthesis. The stem 80 includes a shaft 82 having a top end 84 and a bottom end 86. The top end 84 includes a tapered portion 88 and an axial threaded bore 90. The tapered portion 88 of the stem is received in the second axial bore 64 of the keel 40. This taper joint can also be provided as a self locking taper. A bolt 92 (FIG. 1) extends through the inner bore 26 of the boss 18 and the portal 66 and threads into the threaded bore 90 of the stem 80 to draw and hold the components together. The head 94 (FIG. 3) of the bolt 92 is recessed into a counter bore 96 formed in the top surface 12 of the tray 10.

Figure 21:
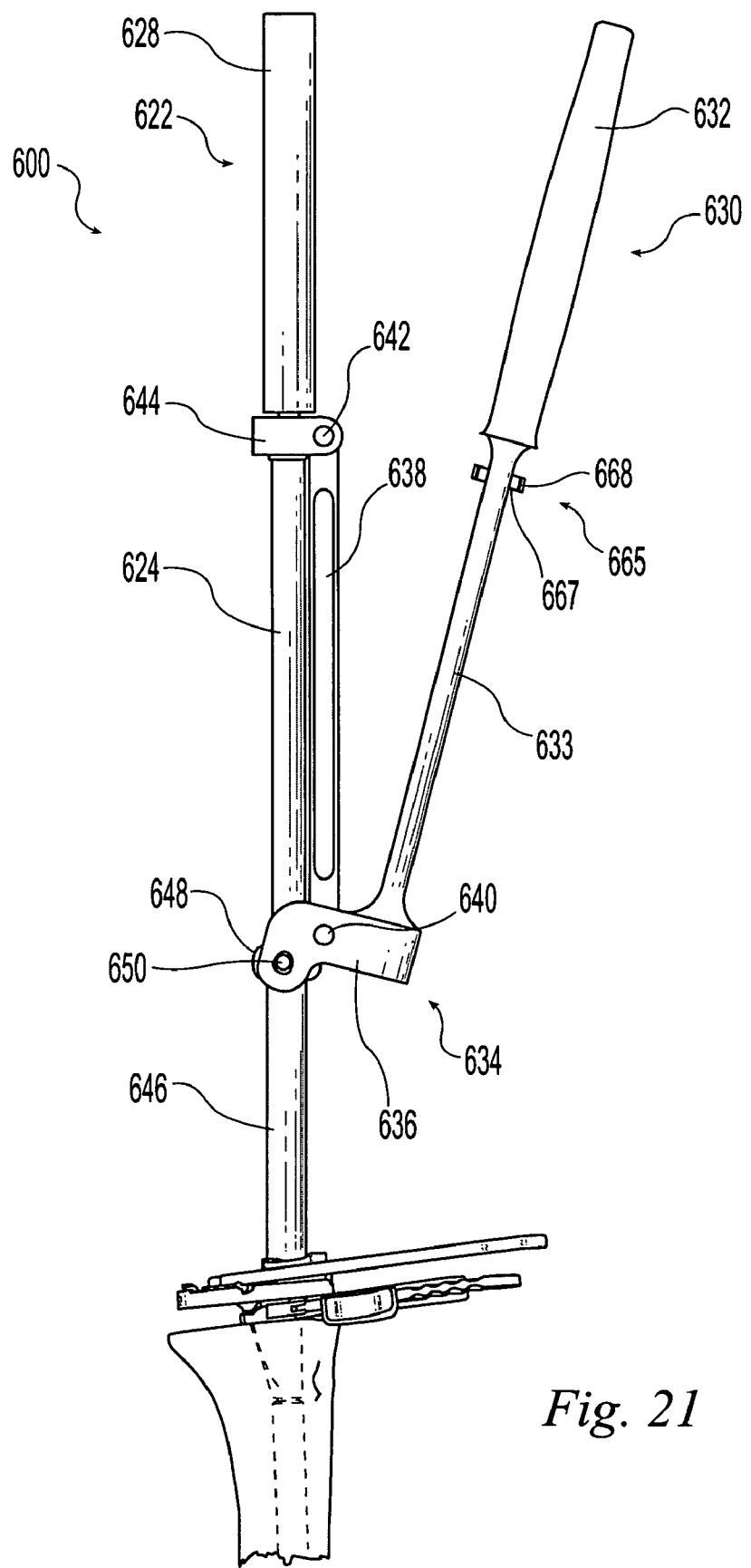
FIG. 21 is a side plan view of an assembly/disassembly tool for assembling and disassembling the keel and tray components.
Figure 22:
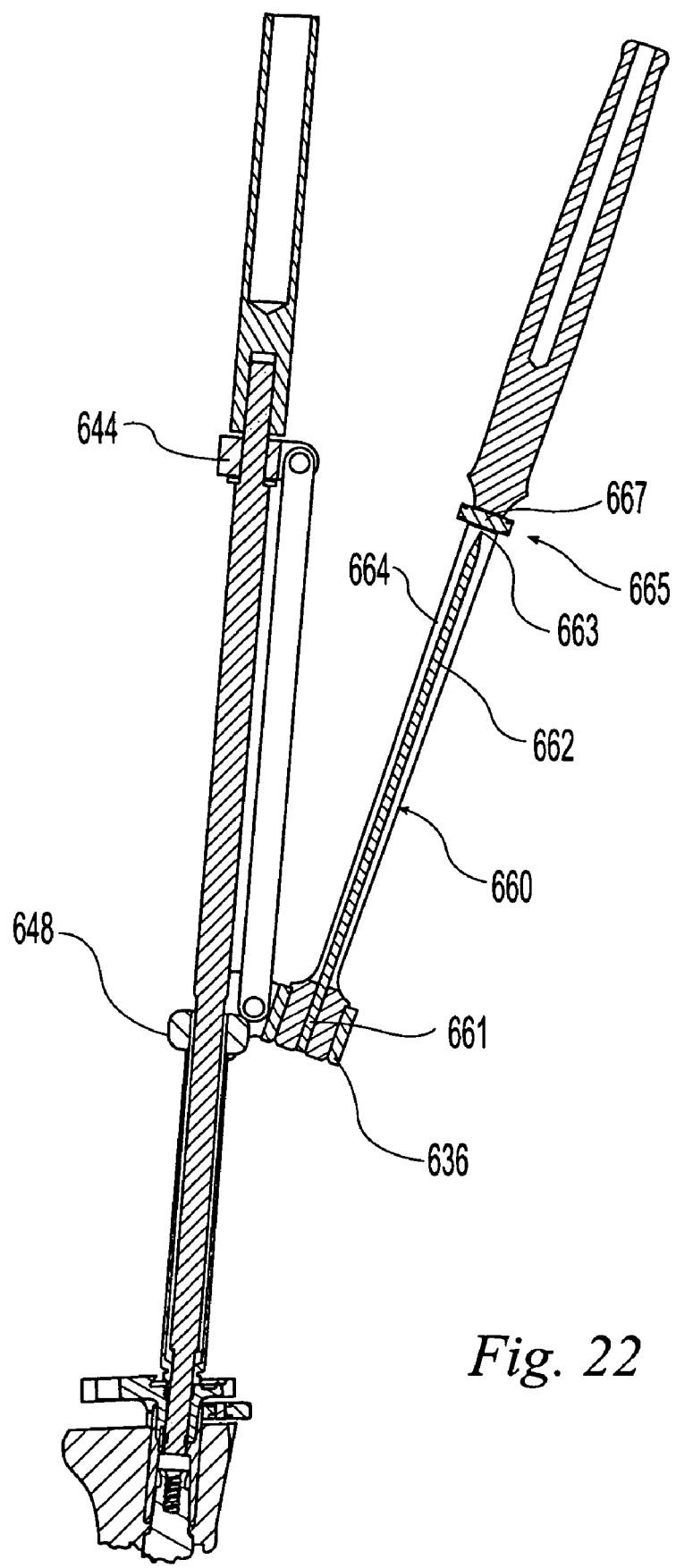
FIG. 22 is a section view of the tool of FIG. 21.
Figure 23:
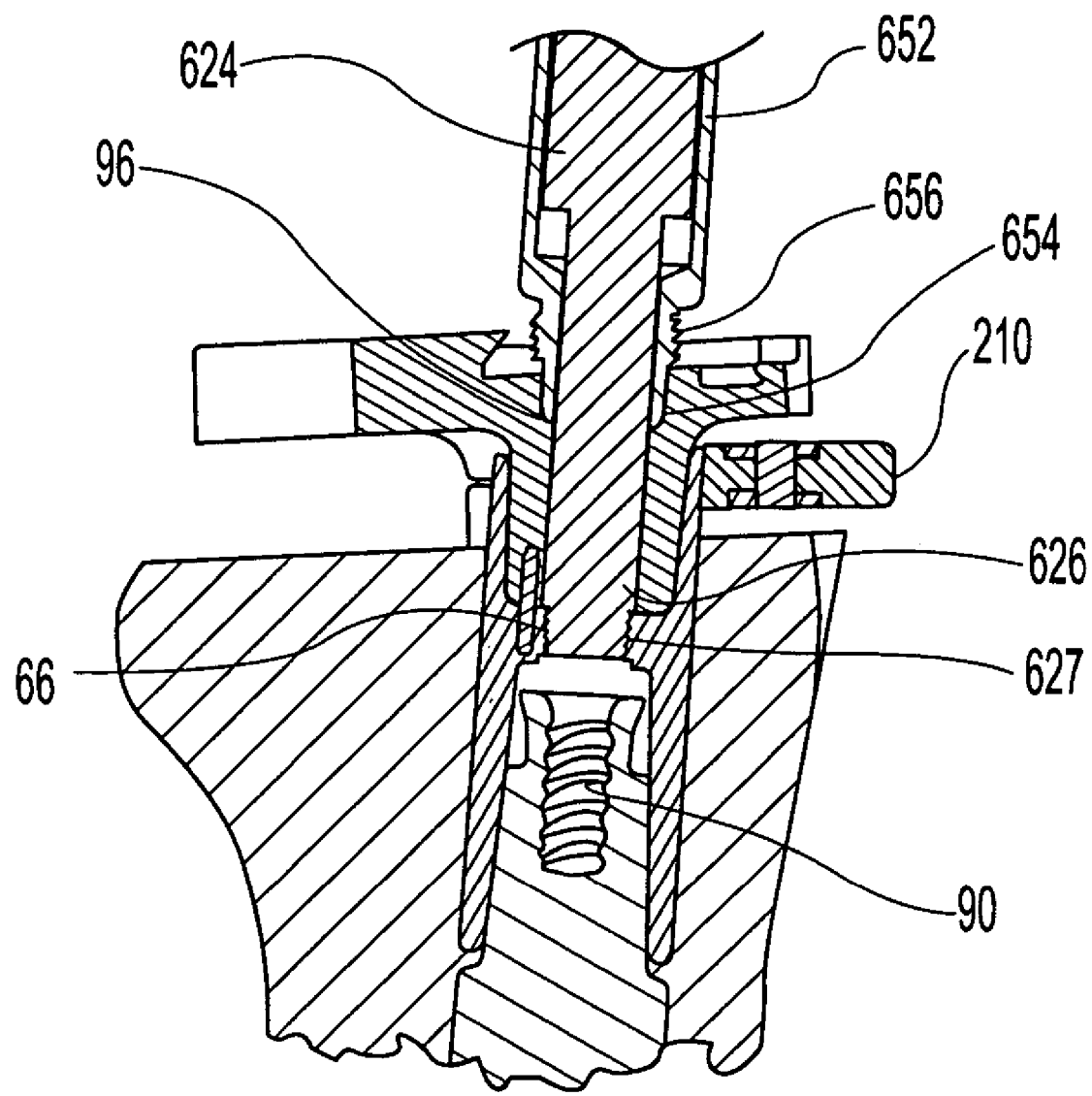
FIG. 23 is a detail view taken from FIG. 22.
Figure 24:
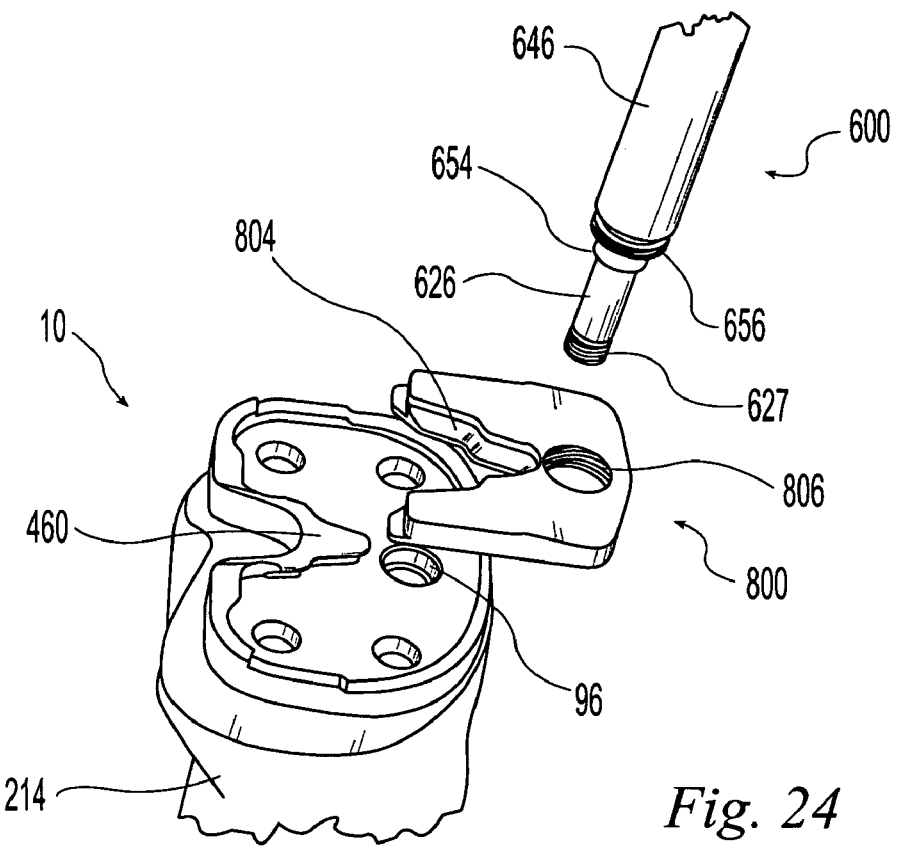
FIG. 24 is an exploded perspective view of a disassembly adapter in use with the assembly/disassembly tool of FIG. 21.
Figure 25:
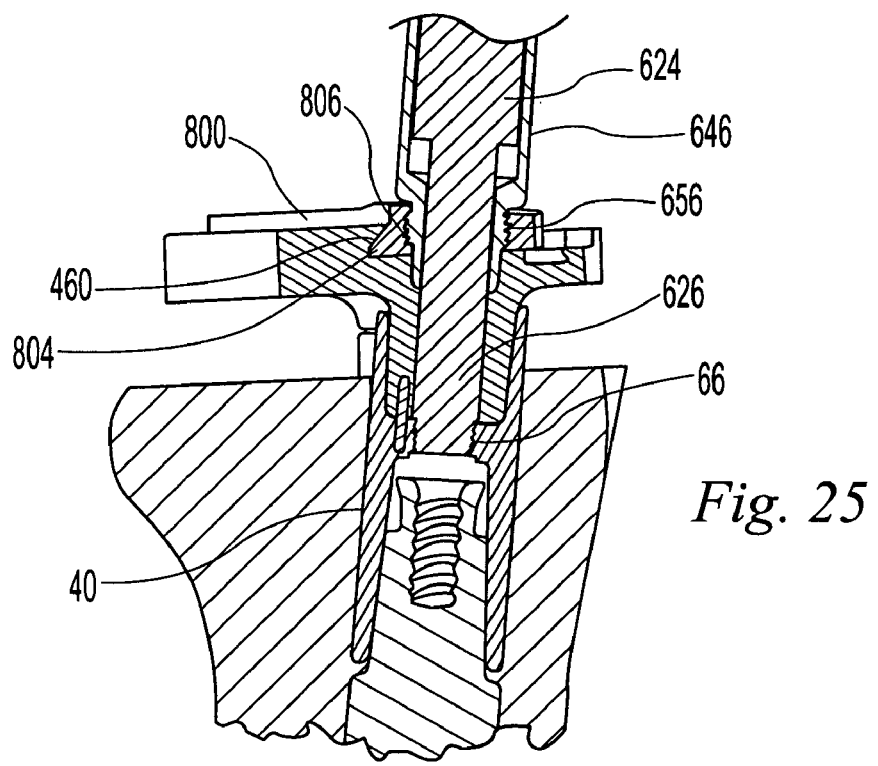
FIG. 25 is a section view of the instruments and implants of FIG. 24.

FIGS. 9-25 illustrate, a set of instruments and their use for handling and assembling the modular implants of this invention. The instruments and methods are applicable to modular implants generally. However, they have features that facilitate minimally invasive surgical procedures. The illustrative instruments are configured for use with the illustrative tibial implant of FIG. 1. FIGS. 9-14 illustrate a tibial keel component holder 210, FIGS. 15-20 illustrate a tibial tray component holder 400, FIGS. 21-23 illustrate an assembly/disassembly tool 600, and FIGS. 24-25 illustrate a disassembly adapter 800 for use with the assembly/disassembly tool 600.

Figure 12:
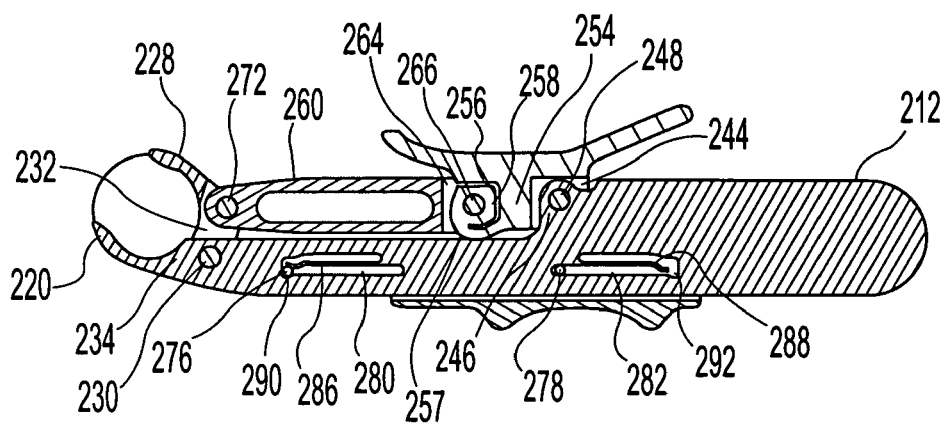
FIG. 12 is a section view of the instrument of FIG. 9 taken along line 11-11 of FIG. 9 and with the cover extended.
Figure 13:
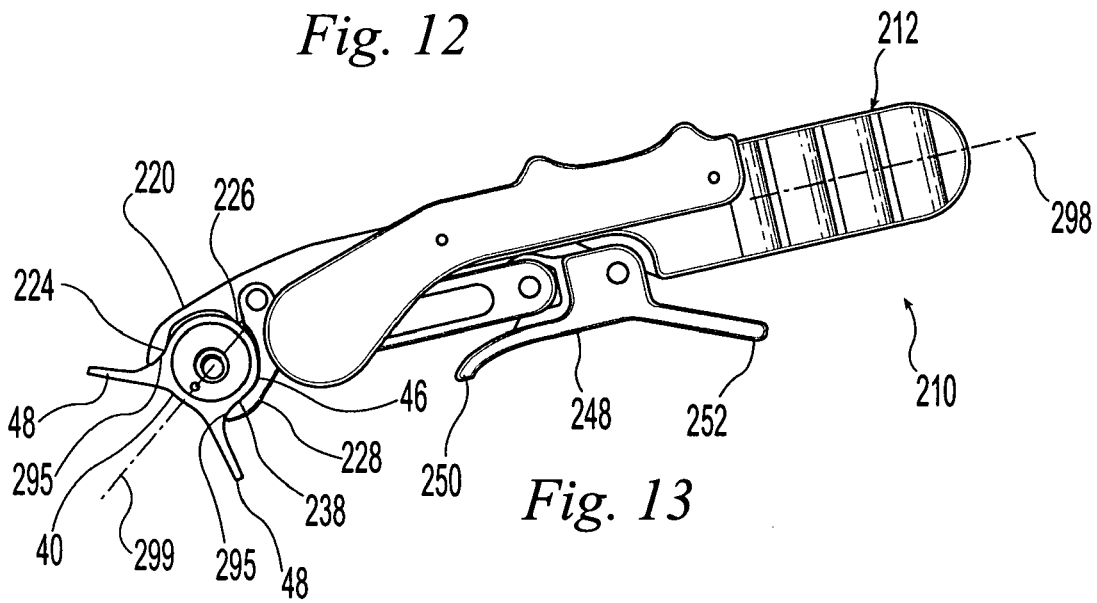
FIG. 13 is a top plan view of the instrument of FIG. 9 in use holding a tibial keel component of a knee prosthesis.
Figure 14:
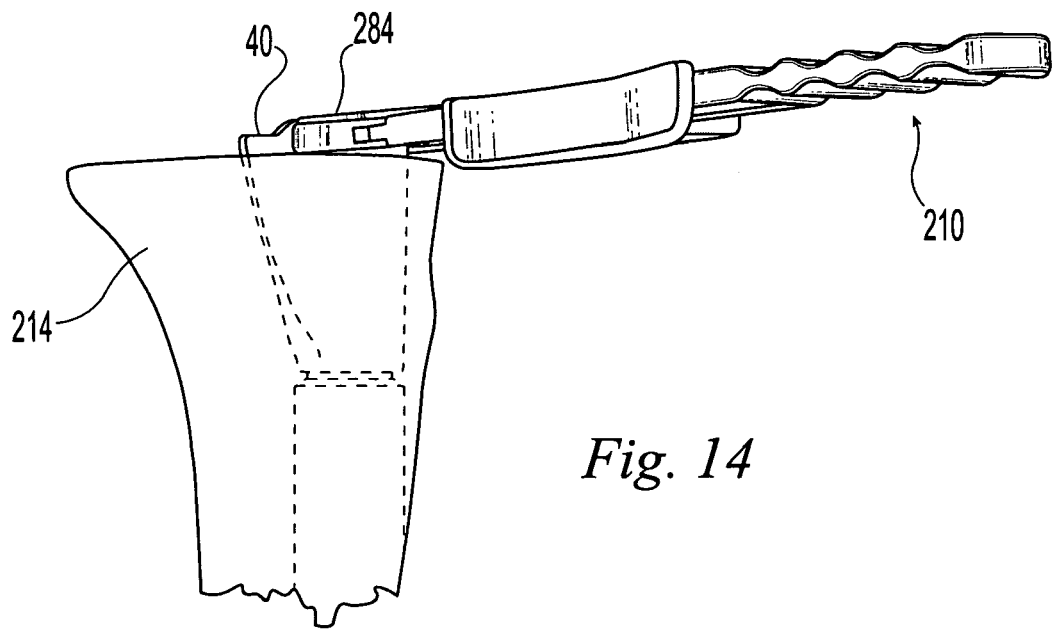
FIG. 14 is a front perspective view of the instrument of FIG. 9 in use holding a tibial keel component of a knee prosthesis.

Turning to FIGS. 9-14, the illustrative keel holder 210 is configured to grip the modular keel 40 to facilitate handling the keel 40 and inserting it into the proximal tibia 214 (FIG. 14). The keel holder 210 includes a cover 274 for protecting the keel holder 210 mechanism and the internal surfaces of the keel 40 from contamination from tissue, fluids, bone cement and other materials that may be present at a surgical site. The keel holder 210 also provides a means for applying a counter torque while bolt 92 is tightened. Finally, observation of the keel holder 210 informs the user of the orientation of the keel 40 even when the keel 40 is not itself visible.

The keel holder 210 includes a handle 212 having a first end 216 for being gripped by a user and a second end 218 forming a fixed jaw 220. Preferably, the handle 212 includes ribs 213 to enhance a user's grip on the instrument. The fixed jaw 220 has an interior curved surface 222 conforming generally to the shape of a portion of the keel and terminating at first 224 and second 226 keel contacting portions.

A pivoting jaw 228 is mounted opposite the fixed jaw 220 for rotation about a jaw/handle pivot pin 230 between a first, open, position in which the pivoting jaw 228 forms a larger angle with the fixed jaw 220 and a second, closed, position in which the pivoting jaw 228 forms a smaller angle with the fixed jaw 220. The pivoting jaw 228 includes a pivot end 231 forming a yoke 232 (FIG. 12) that straddles a portion 234 of the handle 212. The jaw/handle pivot pin 230 passes through the yoke 232 and the portion 234 of the handle 212. The pivoting jaw 228 has an interior curved surface 236 conforming generally to the shape of a portion of the keel and terminating at a third keel contact portion 238.

An actuator 240 (FIG. 9) is mounted on the handle 212 between the first 216 and second 218 ends. The actuator 240 includes a pivot portion 242 forming a yoke 244 (FIG. 12) that straddles an intermediate portion 246 of the handle 212. An actuator/handle pivot pin 248 passes through the actuator yoke 244 and the intermediate portion 246 of the handle 212. The actuator 240 pivots about the actuator/handle pivot pin 248 between a first, closed, position and a second, open, position. The actuator 240 includes first 250 and second 252 input ends spaced from one another on opposite sides of the actuator/handle pivot pin 248. The distance from the actuator/handle pivot pin 248 to each of the first 250 and second 252 input ends determines the mechanical advantage and resulting torque associated with pressing on the first 250 and second 252 input ends. The actuator 240 further includes an output portion 254 (FIG. 12). The output portion 254 includes a "C"-shaped cut 256 defining a cantilevered spring 258. The output portion 254 further has a curved stop surface 257 that contacts the handle 212 to limit how far the actuator 240 can rotate toward the handle 212.

A link 260 connects the actuator 240 to the pivoting jaw 228. The link 260 has a first end 262 forming a yoke 264 that straddles the cantilevered spring 258 of the output portion 254 of the actuator 240. The link 260 is pivoted to the actuator 240 by a link/actuator pivot pin 266 passing through the link yoke 264 and the cantilevered spring 258. The link 260 has a second end 268 forming a tab 270 that fits within the yoke 232 (FIG. 12) of the pivoting jaw 228 and is held in place by jaw/link pivot pin 272.

In the configuration shown in the illustrative embodiment, pressing the first end 250 of the actuator 240 causes the actuator 240 to rotate about the actuator/handle pin 248 and move the output portion 254 forward toward the jaws 220, 228. This in turn causes the link 260 to rotate and move forward to move the pivoting jaw 228 into the closed position. Pressing the second end 252 of the actuator reverses this motion so that the link 260 moves the pivoting jaw 228 to the open position.

A cover 274 (FIG. 9) is in the form of a "U"-shaped member that wraps around one side of the handle 212. The cover 274 is held on the handle 212 by front 276 and rear 278 pins (FIG. 11) pressed through the cover 274. The pins 276, 278 engage front 280 (FIG. 12) and rear 282 longitudinal slots in the handle 212. The cover 274 can slide longitudinally along the handle 212 between a retracted position shown in FIG. 9 and an extended position shown in FIG. 10. The cover 274 includes an extension 284 (FIG. 10) extending forward along one side of the handle 212. The extension 284 conforms generally to the shape of the jaws 220, 228 such that when the cover is extended it encloses, or covers, the space between the jaws 220, 228 on one side. The cover 274 further includes projections 294 extending outwardly to create a thumb grip surface 296 for manipulating the cover 274 between the retracted and extended positions. The front 280 and rear 282 longitudinal slots are formed in the handle 212 so as to create cantilevered springs 286, 288 and detent notches 290, 292 opposite the springs 286, 288. When the cover 274 is slid fully back into the retracted position, the rear cover pin 278 is biased into the rear detent notch 292 by the rear cantilevered spring 288 which holds the cover 274 in the retracted position. Thumb pressure against the projections 294 can overcome the spring tension holding the rear pin 278 in the rear detent notch 292 and cause the cover to slide forward. As it reaches the extended position, the front cover pin 276 is biased into the front detent notch 290 by the front cantilevered spring 286 which holds the cover 274 in the extended position.

In use, the cover 274 of the keel holder 210 is placed in the extended position to serve as a positioning reference and to protect the internal surfaces of the keel. The jaws 220, 228 are positioned around the outer wall 46 of the keel 40 as shown in FIG. 13. The cover 274 is shown retracted in FIG. 13 so that the jaw positions can be seen. However, when positioning the keel holder 210 on the keel 40, the cover 274 rests on the top end 42 of the keel 40 to establish the vertical position of the jaws 220, 228 relative to the keel 40 as shown in FIG. 14. The jaws 220, 228 conform generally to the shape of the keel 40. The first contact portion 224 on the fixed jaw 220 fits into the radius 295 between the outer wall 46 of the keel 40 and the fin 48 on one side of the keel 40 and the third contact portion 238 on the pivoting jaw 228 fits into the radius 295 between the outer wall 46 of the keel 40 and the fin 48 on the other side of the keel 40. The second contact portion 226 on the fixed jaw 220 contacts the outer wall 46 of the keel 40 between the two radii 295. With the cover extension 284 establishing the vertical position and the first 224 and third 238 contact portions establishing the circumferential orientation, the keel holder 210 can be attached to the keel 40 in the same position each time. As the first end 250 of the actuator 240 is pressed forward, the jaws 220, 228 tighten against the keel 40. Increasing pressure results in further rotation of the actuator 240 and link 260 due to flexing of the various parts of the mechanism. This flexing can be controlled by careful design of the part shapes and careful control of manufacturing tolerances. However, by including the spring 258 on which the link/actuator pin 266 is mounted, a larger amount of flex can be designed into the system due to the deformation of the spring 258. This permits a wider range of size tolerance in the individual parts and results in a more repeatable function and a lower manufacturing cost. When the jaw/link pin 272, link/actuator pin 266, and actuator/handle pin 248 align, the mechanism is said to have reached the point of singularity. If the link/actuator pin 266 is rotated any further, so that it passes the point of singularity, the mechanism will begin to self-rotate and release the tension. However, just after the link/actuator pin 266 passes the point of singularity, the actuator stop surface 257 contacts the handle 212 and prevents further rotation. Thus the action is felt as increasing tension to a point where the mechanism snaps into a self locking orientation. The tension in the mechanism holds the jaws in the closed, or locked, position. To release the jaws, pressure is applied to the second end 252 of the actuator to rotate the actuator stop surface 257 away from the handle 212. Increasing pressure on the actuator 240 rotates it back to the point of singularity again. As the mechanism passes the point of singularity, it self-rotates to the open position with a snap.

With the keel holder 210 locked onto the keel 40, it can be used as a handle to position the keel in the surgical incision and maneuver it down into the bone as shown in FIG. 14. The cover extension 284 covers the first axial bore 50 of the keel 40 to protect it from contamination when the keel 40 is passed through the incision and placed in the bone. The cover also prevents bone cement that has been placed on the bone from extruding over the edge of the keel 40 and contaminating axial bore 50. Furthermore, the keel holder 210 grips the keel 40 along the sides of the keel 40 and thus prevents it from being seated fully into the proximal tibia 214 at this stage in the surgery. The keel holder 210 can be removed at this point and the keel 40 fully seated to make more room for the tray 10 to be engaged with the keel 40, or the keel holder 210 can be left in place to hold the keel above the bone cement until the tray 10 is placed on the keel 40.

Because the keel holder 210 locks onto the keel 40 in the same known orientation each time, the handle 212 can also be used as a visual reference as to the keel's orientation on the bone. The handle 212 has a longitudinal axis 298 (FIG. 13) and the jaws 220, 228 have a jaw axis 299. The jaw axis 299 divides the jaws into two equal halves and is oriented so that when the keel holder 210 is locked onto the keel 40, the jaw axis 299 divides the keel 40 into symmetric halves. The angle between the handle axis 298 and the jaw axis 299 is known so that observing the handle 212 orientation indicates the corresponding keel 40 orientation. Both the ability to grip the keel and the ability to note its orientation are especially helpful when placing the implant in a minimally invasive procedure where access and visibility may be limited.

Figure 19:
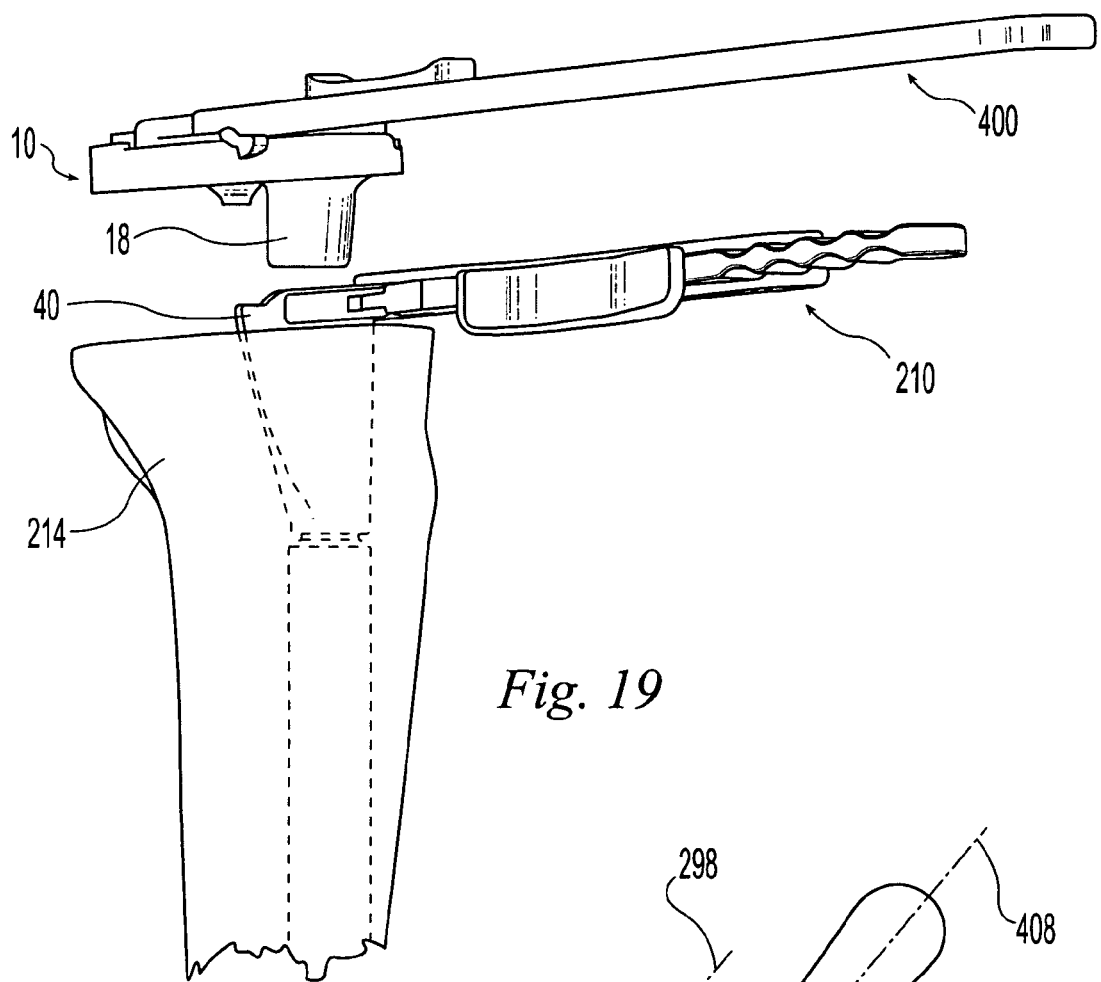
FIG. 19 is a side plan view showing the keel holder of FIG. 9 and the tray holder of FIG. 15 in use.
Figure 20:
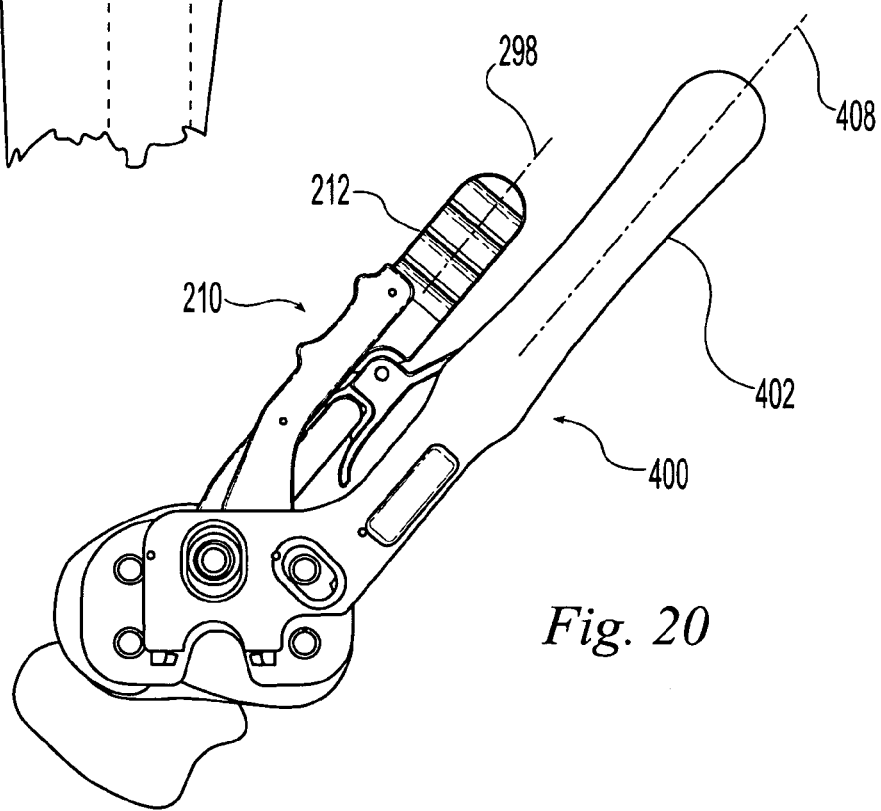
FIG. 20 is a top plan view of the instruments shown in FIG. 19.

Turning to FIGS. 15-20, the illustrative tray holder 400 includes a handle 402 (FIG. 20) and a tray adapter 500 (FIG. 15). The tray holder 400 is configured to grip the modular tray 10 to facilitate handling the tray 10 and inserting it onto the proximal tibia 214 (FIG. 19). The holder 400 also provides a means for applying a torque to the tray 10 if needed. Finally, observation of the tray holder 400 informs the user of the orientation of the tray 10 even when the tray is not itself visible. In the illustrative embodiment, the tray adapter 500 is shown as a separate piece that can be exchanged to fit different sizes of trays 10; however, it is contemplated that the handle 402 and tray adapter 500 may be combined in a single piece.

The handle 402 includes a grip portion 404 and a head 406. The grip portion 404 is generally a flat bar shape having a longitudinal axis 408 (FIG. 16). The head 406 forms an enlargement extending from one end of the handle 402. The head 406 has a top side 410 (FIG. 15) and a bottom side 412. The bottom side 412 of the head 406 includes a generally "U"-shaped notch 414 having side walls 416 (FIG. 17), a back wall 418, and an open front 420 (FIG. 15). The notch 414 has a longitudinal head axis 422 (FIG. 17) extending from back to front. The head axis 422 and grip axis 408 are at a known angle to one another. The side walls 416 include rails 424 (FIG. 15) projecting into the notch 414 and extending parallel to the head axis 422. First 426 (FIG. 16) and second 428 holes extend through the head 406 from top 410 to bottom 412. First 434 and second 436 pins extend from the bottom side 412 into the notch 414.

A slide 438 (FIG. 17), for engaging the tray 10, is recessed in a groove 440 in the bottom side 412 of the grip 404 parallel to the grip axis 408. A slide button 442 (FIG. 16) extends through an elongated hole in the grip 404 so that a user can move the slide 438 along the groove 440 with thumb pressure. One end of the slide 438 includes a presser foot 444 (FIG. 17) projecting toward the head 406. A slide retaining plate 446 overlies the slide 438 to retain it in the groove 440 and is held in place with a slide plate pin 448.

The illustrative modular tray adapter 500 is configured to engage the tray 10 and the handle 402. The tray adapter 500 locks onto the tibial tray 10 via the mechanism used to attach a tibial bearing component onto the tray 10. In the illustrative example, the tray adapter 500 locks onto a dovetail 460 formed on the illustrative tray 10. However, it is contemplated that the tray adapter 500 may engage the tray 10 using any number of mechanisms including for example, bolting to the tray, snapping onto the tray, clamping the tray, and any other suitable mechanism. The tray adapter 500 is generally in the form of a "U"-shaped plate-like body having an outer periphery for engaging the notch 414 formed in the head 406 and an inner periphery for engaging the dovetail 460 formed on the top side of the tray 10. The adapter 500 has a top surface 504, a bottom surface 506, side edges 508, a back edge 510, and a front edge 512. Grooves 514 formed along each side 508 engage the rails 424 in the head 406 to hold the adapter 500 in the head 502. Cantilevered springs 516 (FIG. 18) are defined by spaced apart slots 518 cut through the adapter 500 from the top 504 to the bottom 506. The end of each spring 516 includes a scallop 520. The adapter 500 slides into the notch 414 from the front with the grooves 502 sliding over the rails 424 and is retained by a snap lock. As the back edge 510 of the adapter 500 nears the back wall 418 of the notch 414, the springs 516 abut the pins 436 extending into the notch 414. Sliding the adapter 500 further into the head 406 causes the springs 516 to deflect inwardly until the scallops 520 are reached at which point the springs bias the scallops 520 against the pins 436. The engagement of the scallops 520 and pins 436 keeps the adapter 500 from sliding out of the head 406. To remove the adapter 500, the user must apply enough forward directed force to flex the springs 516 outwardly and disengage the scallops 520 from the pins 436.

The adapter 500 engages the tray 10 with a dovetail notch 530 having a shape complimentary to the dovetail 460 on the tray 10. A cantilevered spring 532 is formed on each side of the dovetail notch 530 by spaced apart slots 534 cut through the adapter 500 from the top 504 to the bottom 506. A pin 536 is pressed into the end 538 of each spring 532 and projects upwardly. A through hole 540 is formed through the adapter from the top 504 to the bottom 506. The adapter 500 is attached to the tray by sliding the adapter 500 down and back so that the dovetail notch 530 engages the dovetail 460 on the tray 10. As the adapter 500 nears the fully seated position, the pins 536 in the springs 532 abut the edge 462 of the tray dovetail 460 causing the springs 532 to flex outwardly. As the pins 536 reach the recesses 464 behind the dovetail 460, the springs 532 bias the pins 536 inwardly to engage the recesses 464 and retain the adapter on the tray 10. When the adapter 500 is fully engaged on the tray 10, the through hole 540 aligns with the inner bore 26 of the tray 10 to permit other instruments and implants to pass through the tray holder 400 and into the tray 10 and keel 40. To remove the adapter from the tray, the user must apply enough outwardly directed force to flex the springs 532 outwardly and disengage the pins 536 from the recesses 464.

In use, the appropriate size tray adapter 500 is selected and slid into the head 406 of the tray holder handle 402 until it snaps in place. The tray adapter 500 and handle 402 assembly is then attached to the tray 10 by sliding the dovetail notch 530 into engagement with the tray dovetail 460 until it snaps in place. The tray holder 400 may then be used to manipulate the tray 10 into position as shown in FIGS. 19 and 20. By applying thumb pressure to the slide button 442, the presser foot 444 of the slide 438 may be biased against the edge 466 of the tray 10 to hold the tray in tight engagement with the tray holder 400.

The angle of the keel holder 210 handle axis 298 relative to the keel 40 and the angle of the tray holder 400 handle axis 408 relative to the tray 10 may be coordinated so that the handles 212, 402 give a visual indication of proper tray-to-keel alignment. For example, in the illustrative embodiment of FIG. 20, the handle axes 298, 408 are designed to be offset and parallel when the tray 10 and keel 40 are properly aligned. By setting the handles 212, 402 parallel, the user is assured that the components are properly oriented relative to one another even if he cannot see the components. By using the handles for tray-to-keel rotational alignment, the rotational alignment pin 73 may be omitted. As the tray 10 is positioned over the keel 40, the cover 274 is slid back to expose the keel bore 50 and allow the tray 10 to be seated.

Turning to FIGS. 21-23, an assembly tool 600 is provided to seat the tray 10 and keel 40 components relative to one another. The tool 600 includes a stationary handle 622 having a shaft 624 terminating in an engagement end 626 and a grip end 628. The engagement end 626 is configured to engage the keel 40 in axial force transmitting relationship. The engagement end 626 may be "T"-shaped to engage the bayonet style portal 66 of FIG. 8 or it may be threaded to engage the threaded portal 66 of FIG. 5. Other suitable connection mechanisms may also be used. Alternatively, the engagement end may extend through the portal 66 and engage the stem 80 such as by threading into the axial threaded bore 90. In the illustrative example, the engagement end 626 includes threads 627 for engaging a threaded portal 66 in the keel 40 in axial force transmitting relationship. A pivot handle 630 includes a grip end 632, a shaft 633, and a working end 634. The working end 634 includes an L-shaped pivot block 636. The pivot block 636 is connected to the stationary handle 622 via a connecting link 638. The connecting link 638 is pinned at one end to the pivot block 636 to form a fulcrum 640 and pinned 642 at the other end to a mounting ring 644 affixed to the stationary handle 622. An engagement member 646 is mounted adjacent the engagement end 626 of the stationary handle 622 and is movable relative to the engagement end 626. In the exemplary embodiment, the engagement member 646 is a sleeve coaxially mounted on the engagement end 626 for longitudinal translation relative to the engagement end 626. A first end 648 of the engagement member 646 is linked to the pivot block 636 and thus to the working end 634 of the pivot handle 630 by a connecting pin 650. A second end 652 of the engagement member 646 includes a nipple 654 that engages the counter bore 96 formed in the top surface 12 of the tray 10. The second end 652 also includes threads 656 for engaging a disassembly adapter 800 described below.

An indicator 660 includes a pointer 662 having a first end 661 attached to the pivot handle 630 near the working end 634 and a second end 663 cantilevered away from the working end 634. The pointer 662 extends adjacent the pivot handle shaft 633. In the illustrative embodiment, the pivot handle shaft 633 includes a longitudinal channel 664 in which the pointer 662 is positioned. The pivot handle shaft 633 includes a scale 665 adjacent the second end 663 of the pointer 662. In the example, the scale 665 comprises a post 667 projecting from the shaft 633 and including an indicia mark 668.

In use, the tray 10 is positioned over the keel 40 as shown in FIGS. 19 and 20, and the boss 18 of the tray 10 is inserted into the first axial bore 50 of the keel. The engagement end 626 of the stationary handle 622 is inserted through the first hole 426 in the tray holder 400, through the inner bore 26 of the boss 18, and threaded into the threaded portal 66 of the keel. If the handles 622, 630 are held loosely, the pivot handle 630 will swing away from the stationary handle 622 as the nipple 654 of the engagement member 646 presses against the bottom of the counter bore 96 in the tray 10. This separation of the handles 622, 630 is a result of the engagement member 646 sliding back along stationary handle shaft 624. As it moves back, it pivots the pivot block 636 and thus the pivot handle 630 about the fulcrum 640. By connecting the pivot block 636 via the elongate connecting link 638, the fulcrum 640 is permitted to move up and down slightly to prevent binding of the mechanism. Once the engagement end 626 securely engages the keel 40, the handles are brought together to seat the keel 40 and tray 10 components. Forcing the handles together moves the engagement member 646 outwardly relative to engagement end 626. The nipple 654 presses against the tray 10 and the engagement end 626 of the stationary handle prevents the keel 40 from moving. The resulting oppositely directed forces on the tray 10 and keel 40 seat the tray 10 and keel 40 tightly together.

The coaxial arrangement of engagement member 646 and engagement end 626 is advantageous since it uniformly loads the junction with a centrally aligned force through the portal 66 and a uniform annular force against the shoulder counter bore 96.

The axial arrangement of the handles in the illustrated embodiment is advantageous in that it allows for an elongate narrow tool. This configuration facilitates entry into narrow confines such as when the tool is used to seat implant components in-situ. In addition, the axial handle arrangement allows for large seating forces to be generated due to the relatively long distance from the grips 628, 632 to the fulcrum 640 and the relatively short distance from the fulcrum 640 to the connecting pin 650. The axial arrangement further contributes to high force capacity since a two-handed grip can be employed to make use of the entire upper body strength of the user if necessary.

Force applied to the pivot handle 630 tends to flex the pivot handle shaft 633. Since the pointer 662 is cantilevered away from the working end 634, it does not flex with the pivot handle shaft 633. The amount of deflection of the pivot handle shaft 633 relative to the pointer 662 is a function of the amount of force applied to the handles and consequently is a function of the opposing forces applied to seat the tray 10 and keel 40. By operating the handles to produce a predetermined relative deflection, a predetermined junction seating force may be reproducibly applied. The scale 665 provides a convenient way to measure handle deflection. When the pointer 662 is aligned with the indicia mark 668 on the post 667 a predetermined force is applied. When the junction assembly tool is not in use, the pointer 662 is housed in the channel 664 which protects against damage to the pointer and its surroundings.

After the tray 10 and keel 40 are seated, the assembly tool 600 is removed. The bolt 92 may now be inserted through the first hole 426 in the tray holder 400, through the inner bore 26 of the boss 18, through the portal 66, and into the threaded bore 90 of the stem to draw and hold the components together. The tray holder 400 allows the user to impart a counter-torque on the tray 10 while the bold is tightened to prevent the implant from rotating out of position. Bone screws may also be inserted through the fixation holes 36 in the tray and threaded into the proximal tibia 214. The second hole 428 in the tray holder head 406 allows access to one of the fixation holes 36 that would otherwise be covered.

The exemplary embodiment has illustrated a tool for seating implant components. FIGS. 24 and 25 illustrate an adapter 800 to permit the tool to be used for unseating the components. As shown in FIG. 23, the nipple 654 on the second end 652 of the engagement member 646 presses against the counter bore 96 to seat the components. If the handles are then moved apart, the nipple 654 retracts away from the counter bore 96 since the pressing engagement of the nipple 654 with the counter bore 96 is not bi-directional. This is in contrast to the bi-directional engagement of the threaded engagement 627 of the stationary handle 622 with the threaded portal 66 of the keel. If, on the other hand, the second end 652 is enabled to engage the tray 10 for applying an upward force, then moving the handles apart would cause the joint components to move out of their seated arrangement. The adapter 800 allows the second end 652 to engage the tray 10 in upward pulling relation. The adapter 800 has a generally plate-like body having a dovetail cutout 804 complimentary to the tray 10 dovetail 460. The adapter further includes a threaded through bore 806 that aligns with the counter bore 96 of the tray 10. In use, the adapter 800 is slipped onto the tray 10 with the adapter dovetail 804 underneath and engaging the tray dovetail 460. The threaded through bore 806 of the adapter 800 aligns with the counter bore 96 of the tray 10. The threaded engagement end 626 of the stationary handle 622 of the assembly tool 600 is inserted through the through bore 806 and threaded into the portal 66 between the first 50 and second 64 axial bores of the keel 40. The threads 656 of second end 652 of the engagement member 646 are threaded into the threaded through bore 806 in the adapter 800. Since the end 626 of the stationary handle 622 passes through the threaded through bore 806, it prevents the adapter 800 from sliding away from and disengaging the dovetail 460. As the handles 622, 630 are pulled apart, the engagement member 646 is lifted relative to the engagement end 626 of the stationary handle 622. The engagement member 646 transmits this lifting force to the adapter 800 through the threads 656 to the threaded through bore 806. The adapter 800 presses upwardly on the tray dovetail 460 while the stationary handle 622 presses downwardly on the keel 40 thus disassembling the tray 10 and keel 40.

In clinical use, an incision is made in the knee joint. For a minimally invasive surgical approach according to the present invention, an incision is made that avoids compromising the soft tissue of the suprapatellar pouch. Next, resection instruments are introduced through the incision to prepare the proximal tibial bone and form a keel receiving recess. Ideally, only the minimum amount of bone required to provide a stable flat surface on the tibia is removed. The illustrative modular tibial component has a low profile. Because of this low profile and modularity, the incision can be quite small and need only be large enough to allow passage of the individual components. The present investigators have found that a tray component having an overall height less than 18 mm can be inserted through such a minimally invasive surgical incision and engage the tibia where the minimum amount of bone has been removed. The keel component of the present invention can be manipulated into the prepared joint space because it lacks the large top surface of the tray. Likewise, the low profile and modularity of the components permit the patella to remain in its anatomic orientation relative to the femur to further reduce the trauma experienced by the joint during surgery and aid recovery and ultimate outcome from the procedure. The keel is manipulated through the incision and placed into the recess. The tray is then manipulated through the incision and engaged with the keel. The tray and keel holders facilitate manipulating the components into the prepared space and may be used to indicate the component orientations even if the components themselves are hidden from view. The assembly instrument is engaged with the tray and keel and activated to draw the components together to engage the press-fit and seat the modular junction.

It will be understood by those skilled in the art that the foregoing has described illustrative embodiments of the present invention and that variations may be made to these embodiments without departing from the spirit and scope of the invention defined by the appended claims. The various aspects of the present invention are applicable to a variety of bone implants in addition to the illustrative tibial implant. Likewise, where male/female engaging portions have been depicted, the male and female components may be reversed and still be within the scope of the invention.

What is claimed is:

1. An instrument for gripping a tibial keel component of a modular keel and tray assembly, the keel component having a first end and a second end, the keel component being configured for insertion of the second end into a tibial bone, the instrument comprising:
 a handle;
 a clamp for connecting the instrument to the keel, the clamp being connected to the handle and having a top surface and an opposing bottom surface, the clamp having a first position in which the clamp applies a clamping force to the keel component to lock the keel component to the instrument and the handle extends outwardly from the keel component to provide a grip for manipulating the keel component, the clamp having a second position in which the keel component is moveable relative to the clamp; and a cover, with the clamp in the first position in which the clamp applies a clamping force to the keel component and with the keel component extending from the bottom surface of the clamp, the cover is moveable to selectively position the cover over the first end of the keel component to shield the first end of the keel component from contamination while the second end of the keel component extends from the bottom surface of the clamp and is engageable with a tibial bone, the cover movable while the instrument is connected to the keel component between a first position in which the cover is positioned over the portion of the keel component and a second position in which the cover is positioned away from the portion of the keel component to expose the keel component.

2. The instrument of claim 1 wherein the clamp connects the instrument to the keel component in a reproducible known orientation such that the orientation of the handle indicates the orientation of the keel component even when the keel component is not itself visible.

3. The instrument of claim 1 wherein the clamp further comprises:

a first jaw attached to the handle; and a second jaw attached to the handle, the jaws being movable relative to one another to clamp the keel component.

4. The instrument of claim 1 wherein the clamp further comprises:

an actuator;

a link connecting the actuator to the jaws, the actuator being movable to cause the jaws to move between a closed position in which they are relatively close together and an open position in which they are relatively further apart, the actuator, link, and jaws having a point of singularity beyond which further movement of the actuator results in the jaws locking onto the keel in the closed position.

5. The instrument of claim 1 wherein the cover is lockable in both the first and second positions.

6. The instrument of claim 1 wherein the clamp connects the handle to the first end of the keel component such that upon insertion of the second end of the keel component into the tibial bone, at least one of the attachment mechanism and handle abut the tibial bone and prevent the first end of the keel component from being fully inserted into the tibial bone.

7. A tibial keel holder and tibial tray holder combination, the tibial keel holder being engageable with a tibial keel component of a modular tibial implant, the tibial keel component having a first end and a second end, and the tibial tray holder being engageable with a tibial tray component of a modular tibial implant, the tibial keel component and tibial tray component forming a male/female junction between them, the combination comprising:

a tibial keel holder including a first handle, a clamp for connecting the tibial keel holder to the tibial keel component in a reproducible known orientation, and a cover, the clamp being connected to the handle and having a top surface and an opposing bottom surface, the clamp having a first position in which the clamp applies a clamping force to the tibial keel component to lock the tibial keel component to the tibial keel holder, the clamp having a second position in which the tibial keel component is moveable relative to the clamp, with the clamp in the first position in which the clamp applies a clamping force to the keel and with the second end of the tibial keel component extending from the bottom surface of the clamp, the cover is moveable to selectively position the cover over the first end of the tibial keel component to shield the first end of the tibial keel component from contamination while the second end of the tibial keel component extends from the bottom surface of the clamp and is engageable with a tibial bone;

a tibial tray holder including a second handle and an attachment mechanism for connecting the tibial tray holder to the tibial tray component in a reproducible known orientation, the first and second handles forming a predetermined angle between them to give a visual indication of tray-to-keel rotational alignment; and an assembly tool for moving the tibial tray component and the tibial keel component into male/female seating arrangement, the assembly tool being engageable with the tibial tray component and the tibial keel component while the tibial tray holder is holding the tibial tray, the assembly tool passing through an opening in tibial tray holder to engage the tibial tray component and the tibial keel component while the tibial tray holder is holding the tibial tray.

8. The combination of claim 7 wherein the proper tray-to-keel alignment is indicated when the first and second handles are parallel to one another.

* * * * *